United States Patent [19]

Kaiser

[11] Patent Number: 5,248,792

[45] Date of Patent: Sep. 28, 1993

[54] 5-METHYL-6-PENTYL-TETRAHYDRO-α-PYRONE AND ANALOGS

[75] Inventor: Roman Kaiser, Uster, Switzerland

[73] Assignee: Givaudan-Roure Corporation, Clifton, N.J.

[21] Appl. No.: 882,403

[22] Filed: May 13, 1992

[30] Foreign Application Priority Data

May 15, 1991 [CH] Switzerland ............... 1450/91
Mar. 18, 1992 [CH] Switzerland ............... 876/92

[51] Int. Cl.$^5$ ............................................. C07D 309/00
[52] U.S. Cl. .................................. 549/273; 512/11
[58] Field of Search ........................... 512/11; 549/273

[56] References Cited

U.S. PATENT DOCUMENTS 4,212,773  7/1980  Schaper et al. ............... 512/11
4,257,923  3/1981  Escher ........................ 512/11

FOREIGN PATENT DOCUMENTS 41-8341    4/1966  Japan ......................... 549/273
55-120579  9/1980  Japan ......................... 549/273
58-13572   1/1983  Japan ......................... 549/273

OTHER PUBLICATIONS

Lloyd et al. Chem. Abst., vol. 85, #59847q (1976).
Girardon et al., Chem. Abst., vol. 104, #145522x (1986).
Pyysalo et al., Chem. Abst., vol. 84, #69087k (1976).
Chemical Abstract 96:52059C for R. Schlessinger et al., J. Am. Chem. Soc. 104 (1982) p. 357 ff.
Chemical Abstract 97:109749e for R. Wood et al., Tett. Lett. 23 (1982) p. 707 ff.
Chemical Abstract 105:226136x for R. Schlessinger et al., J. Org. Chem. 51 (1986) p. 3070 ff.
Chemical Abstract 108:186376d for T. Tanaka et al., Chem. Pharm. Bull. 35 (1987) p. 2209 ff.
Chemical Abstract 109:210832t for J. Whitesell et al., J. Org. Chem., 53 (1988) p. 5383 ff.
Chemical Abstract 111:153468u for F. Kazmierczak et al., J. Org. Chem. 54 (1989) p. 3988 ff.
D. Collum et al., J. Am. Chem. Soc. 105 (1983) p. 6882 ff.
J. Rocca et al., Tett. Letters 24 (1983) p. 1893 ff.
P. Wuts et al., Tett. Letters 25 (1984) p. 4051 ff.

*Primary Examiner*—James H. Reamer
*Attorney, Agent, or Firm*—Robert F. Tavares; Linda A. Vag

[57] ABSTRACT

The invention concerns odorant and flavorant compositions which contain one or more compounds of the formula

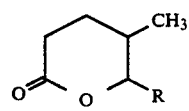

I wherein R represents an alkyl group having from three to eight carbon atoms. The invention also concerns 5-methyl-6-pentyl-tetrahydro-α-pyrone (compound of formula I in which R represents pentyl) in the form of its cis-isomer, its trans-isomer or its cis/trans isomer mixture, and a process for its manufacture by a Bayer-Villiger oxidation of 2-pentyl-3-methyl-cyclopentan-1-one. As fields of use for these compounds there come into consideration, for example, perfume and flavoring compositions, foodstuffs, semi-luxury consumables and drinks.

3 Claims, No Drawings

5-METHYL-6-PENTYL-TETRAHYDRO-α-PYRONE AND ANALOGS

SUMMARY OF THE INVENTION

The present invention concerns odorant and flavorant compositions which contain tetrahydro-α-pyrones of the formula

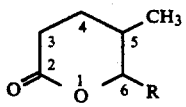

I wherein R represents an alkyl group having from three to eight carbon atoms. The alkyl group may be straight-chain or branched.

The compounds of formula I may exist as stereoisomers due, inter alia, to the methyl substituent at the 5-position of the tetrahydro-α-pyrone ring. It has emerged that one stereoisomer (the cis- or trans-isomer) of a stereoisomeric pair of formula I may have different organoleptic properties when compared with the other stereoisomer. Formula I is intended to embrace, inter alia, these stereoisomeric forms and their mixtures.

Certain compounds of formula I are known per se, but their organoleptic properties have never been described. The 5-methyl-6-pentyl-tetrahydro-α-pyrone (alternate nomenclature: 4-methyl-5-decanolide or 5-methyl-6-pentyl-tetrahydro-α-pyran-(2H)-2-one), I', the compound of formula I wherein R represents pentyl, is a novel compound. Due to the particular organoleptic properties possessed by 5-methyl-6-pentyl-tetrahydro-α-pyrone both the mixture of isomers I' and the cis-isomer of the formula

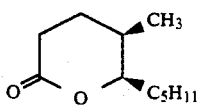

I'a and the trans-isomer of the formula

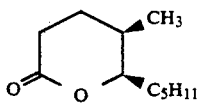

I'b are preferred compounds of formula I. The cis-isomer I'a has a very pleasant and surprising room-filling odor which on the one hand is reminiscent of certain aspects of the smell of the flower of the tuberose (Polianthes tuberosa) and gardenia varieties and on the other hand is reminiscent of caramel, condensed milk and coconut, especially coconut milk. The trans-isomer exhibits similar olfactory characteristics, though somewhat less pronounced; the weaker characteristics are compensated by side aspects. The invention therefore also concerns 5-methyl-6-pentyl-tetrahydro-α-pyrone, I', and a process for its manufacture.

DESCRIPTION OF THE PREFERRED EMBODIMENTS

The process in accordance with the invention for the manufacture of the 5-methyl-6-pentyl-tetrahydro-α-pyrone comprises subjecting 2-pentyl-3-methyl-cyclopentan-1-one to a Bayer-Villiger oxidation in accordance with Scheme I.

SCHEME I

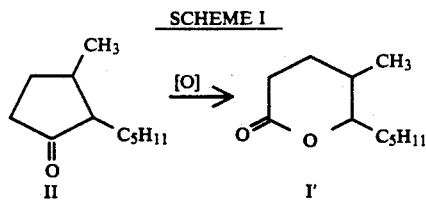

A peracid, for example peracetic acid, trifluoroperacetic acid, perbenzoic acid or monoperphthalic acid, preferably peracetic acid, is used as the oxidizing agent. The reaction is conveniently effected in an inert organic diluent such as methylene chloride, dichloroethane, toluene, xylene, etc. at temperatures between −30° C. and +50° C., preferably in the temperature range of 20° C. to 35° C.

As the starting material there can be used pure cis- or trans-2-pentyl-3-methyl-cyclopentan-1-one, which leads predominantly to cis- or, respectively, trans-5-methyl-6-pentyl-tetrahydro-α-pyrone. A convenient method uses a cis/trans mixture of 2-pentyl-3-methyl-cyclopentan-1-one since a cis/trans mixture can be readily obtained by hydrogenation in a manner known per se of 2-pentyl-3-methyl-2-cyclopenten-1-one (dihydrojasmone) a known perfumery product of the formula

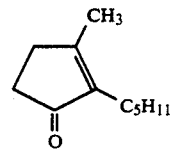

The cis-2-pentyl-3-methyl-cyclopentan-1-one is the primary product of the hydrogenation. Depending on the reaction conditions (solvent, temperature, catalyst etc.) there is formed from the cis-isomer more or less of the corresponding trans compound.

Where a cis/trans mixture of the 5-methyl-6-pentyl-tetrahydro-α-pyrone (compound of formula I) is obtained, this can be separated into the pure cis- and trans-isomers according to methods known per se, for example by chromatographic or distillative procedures.

The yield of olfactorily good material is high for both the hydrogenation and oxidation reaction steps, normally above 75%.

The compound I' (the cis-isomer I'a, the trans-isomer I'b as well as their mixtures) in accordance with the invention and the remaining compounds of formula I are distinguished in general by fragrance notes which are reminiscent of certain aspects of the fragrance of flowers of the tuberose and gardenia varieties, condensed milk, caramel and coconut and also are reminiscent of those of tropical fruits.

With regard to their aforementioned valuable olfactory properties the compounds I are suitable as odorants and/or flavorants, especially in combination with the extensive range of natural and synthetic odorants or flavorants available today for the creation of perfume and flavoring compositions which can be used in all conventional fields of application. Examples of the numerous known odorant ingredients of natural or synthetic origin, whereby the range of the natural raw materials can embrace not only readily-volatile but also moderately-volatile and difficultly-volatile components and that of the synthetics can embrace representatives from numerous classes of substances, are:

- Natural products, such as tree moss absolute, basil oil, tropical fruit oils (such as bergamot oil, mandarine oil, etc.), mastix absolute, myrtle oil, palmarosa oil, patchouli oil petitgrain oil, wormwood oil, lavender oil, rose oil, jasmine oil, ylang-ylang oil, sandalwood oil,
- alcohols, such as farnesol, geraniol, linalool, nerol, phenylethyl alcohol, rhodinol, cinnamic alcohol, cis-3-hexenol, menthol, α-terpineol,
- aldehydes, such as citral, α-hexylcinnamaldehyde, hydroxycitronellal, Lilial ® (Givaudan) (p-tert.butyl-a-methyl-dihydrocinnamaldehyde), methylnonylacetaldehyde, phenylacetaldehyde, anisaldehyde, vanillin,
- ketones, such as allyl ionone, α-ionone, β-ionone, isoraldeine (isomethyl-α-ionone), verbenone, nootkatone, geranylacetone,
- esters, such as allyl phenoxyacetate, benzyl salicylate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate, etc.
- lactones, such as γ-undecalactone, δ-decalactone, pentadecan-15-olide,
- various components often used in perfumery, such as indole, p-menthane-8-thiol-3-one, methyleugenol, eugenol, anethol.

The ordorant compositions produced using compounds I, especially those having a flowery, flowery-spicy, flowery-fruity and flowery-oriental direction, captivate especially by their originality.

When used as odorants the compounds of formula I (or their mixtures) can be employed in wide limits which in compositions can range, for example, from about 0.1 (detergents) to about 30 weight percent (alcoholic solutions) without these values being, however, limiting values, since the experienced perfumer can also achieve effects with even lower concentrations or can synthesize novel complexes with even higher amounts. The preferred concentrations range between about 0.5 and about 10 weight percent. The compositions produced with the compounds I can be used for all kinds of perfumed consumer goods (eau de cologne, toilet water, extracts, lotions, creams, shampoos, soaps, salves, powders, toothpastes, mouth washes, deodorants, detergents, fabric conditioners, tobacco, etc.).

The compounds can accordingly be used for the production of compositions and—as the above compilation shows—using a wide range of known odorants or odorant mixtures. In the production of such compositions the known odorants or odorant mixtures enumerated above can be used according to methods known to the perfumer such as e.g. from W. A. Poucher, Perfumes, Cosmetics and Soaps 2, 7th Edition, Chapman and Hall, London 1974.

As flavorants the compounds I can be used, for example, for the production or improvement, intensification, enhancement or modification of fruit flavors, e.g. mango, passion fruit, peach and coconut. As fields of use for these flavors there come into consideration, for example, foodstuffs (yoghurt, confectionary, desserts, especially desserts based on caramel, etc.), semi-luxury consumables (tea, coffee, tobacco, etc.) and drinks (lemonade etc.).

The pronounced flavor qualities of the compounds I enable them to be used as flavorants in low concentrations. A suitable dosage embraces the range of 0.01 to 100 ppm, preferably of 0.1 to 10 ppm, in the finished product, i.e. the flavored foodstuff, semi-luxury consumable or drink.

The compounds can be mixed with the ingredients used for flavoring compositions or added to such flavorings in the usual manner. Under the flavorings used in accordance with the invention there are to be understood flavoring compositions which can be diluted or distributed in edible materials in a manner known per se. They contain, for example, about 0.01-30, especially 0.1-10, wt. % of flavorant(s) of formula I. They can be converted according to methods known per se into the usual forms of use such as solutions, pastes or powders. The products can be spray-dried, vacuum-dried or lyophilized.

The known flavoring substances which are conveniently used in the production of such flavorings are either already referred to in the above compilation or can be taken readily from the literature such as e.g. J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc. Cleveland, Ohio, 1975.

For the production of such usual forms of use there come into consideration, for example, the following carrier materials, thickeners, flavor improvers, spices and auxiliary ingredients, etc.:

Gum arabic, tragacanth, salts or brewers' yeast, alginates, carrageen or similar absorbents; maltol, spice oleoresins, smoke flavors; cloves, diacetyl, sodium citrate; monosodium glutamate, disodium inosine-5'-monophosphate (IMP), disodium guanosine-5-phosphate (GMP); or special flavoring substances, water, ethanol, propylene glycol, glycerine, etc.

Having regard to their superior olfactory properties the compounds of formula I are preferably used in luxury perfumes and in cosmetic compositions.

The following Examples illustrate the invention.

I. MANUFACTURE OF THE COMPOUNDS OF FORMULAS I', I'A AND I'B

Example 1

Commercially available 2-pentyl-3-methyl-2-cyclopenten-1-one (dihydrojasmone) (78.0 g, 0.47 mol) is dissolved in 90 ml of pure ethanol, treated with 0.50 g of 10% palladium on active charcoal and subsequently hydrogenated at normal pressure and room temperature while stirring intensively until saturated (hydrogen consumption: 12.0 l in 2 hours). The reaction solution is freed from the catalyst by filtration and subsequently concentrated under reduced pressure. Distillation of the crude product (76.0 g) over a distillation column gives 68.0 g of material of b.p.$_{0.12}$ 67°–68° C., which contains in a yield of above 98% cis-2-pentyl-3-methyl-cyclopentan-1-one (IIa) and trans-2-pentyl-3-methyl-cyclopentan-1-one (IIb) in the ratio of 3:2.

The above mixture of IIa and IIb (42.6 g, 0.25 mol) is dissolved in 200 ml of methylene chloride, treated with 34.0 g of anhydrous sodium acetate and subsequently treated with 62.5 g of peracetic acid (40%) in the course of 30 minutes while stirring well and cooling with ice. Subsequently, the ice-cooling is removed and the reaction solution is held in a temperature range of 25°-30° C. by occasional cooling with water at 15° C.

After 1.5 hours an exothermic reaction can no longer be ascertained and analysis by gas chromatography shows the desired conversion of above 95%. The reaction solution is now washed three times with water, three times with sodium sulphite solution (10%) and twice with sodium chloride solution, and the organic phase is dried with anhydrous sodium sulphate and subsequently concentrated under reduced pressure.

Distillation of the thus-obtained crude lactone (41.9 g) over a distillation column gives 35.9 g (78%) of olfactorily good product of b.p.$_{0.05}$ 82°-83° C. consisting of above 97% of cis-5-methyl-6-pentyl-tetrahydro-α-pyrone (cis-4-methyl-5-decanolide, I'a) and trans-5-methyl-6-pentyl-tetrahydro-α-pyrone (trans-4-methyl-5-decanolide, I'b) in the ratio of about 3:2.

The isomers I'a and I'b, characterized hereinafter by their spectral data, are obtained by separating the above-described mixture with the aid of gas chromatography. Isomer I'a shows a somewhat longer retention time than isomer I'b on conventional gas chromatography columns.

cis-5-Methyl-6-pentyl-tetrahydro-α-pyrone (I'a):Infrared spectrum: 1735, 1238, 1200, 1140, 1095, 1069, 1054, 993, 908 cm$^{-1}$;$^1$H-NMR (400 MHz, CDCl$_3$): 0.90 (t,J~7, —CH$_3$), 0.96 (d,J~7, H$_3$C-C(4), 1.25-1.60 (m, together 6H), 1.62-1.72 (m,2H), 1.95-2.10 (m,3H), 2.53 (dxd, J~7, 2H—C(2), 4.28 (m, H—C(5) ppm;mass spectrum (m/e): (M+, 0.2), 128(3), 113(23), 99(3), 95(1), 85(15), 84(39), 69(5), 67.5(5), 57(10), 56(100), 55(24), 43(26), 41(22).

trans-5-Methyl-6-pentyl-tetrahydro-α-pyrone (I'b):Infrared spectrum: 1735, 1248, 1200, 1118, 1098, 1080, 1032, 2020 cm$^{-1}$;$^1$H-NMR (400 MHz, CDCl$_3$): 0.90 (t,J~7, —CH$_3$), 1.00 (d,J~7, H$_3$C—C(4), 1.22-1.64 (m, together 8H), 1.66-1.78 (m,2H), 1.86-1.94 (m,1H), 2.42-2.51 (m, H$_a$—C(2), 2.58-2.65 [m, H$_b$—C(2)], 3.93 [m, H—C(5)] ppm;mass spectrum (m/e): 184 (M+, 0.2), 128(4), 114(10), 113(100), 99(3), 95(2), 85(27), 84(44), 69(8), 67(8), 57(14), 56(100), 55(34), 43(29), 41(26).

In an analogous manner there are obtained:
cis/trans-4-methyl-5-nonanolide, odor: after coconut, celery,
cis/trans-4-methyl-5-undecanolide, odor: sweet, fruity.

II. FORMULATION EXAMPLES

Example 2

Perfume composition in the direction of ylang-ylang containing cis- and trans-5-methyl-6-pentyl-tetrahydro-α-pyrone.

|  | Parts by weight |
|---|---|
| Linalool | 150 |
| Benzyl acetate | 130 |
| Benzyl salicylate | 100 |
| Cinnamyl acetate | 80 |
| Geranyl acetate | 80 |
| Benzyl benzoate | 80 |
| Methyl benzoate | 78 |
| Geraniol | 75 |
| Cinnamic alcohol | 60 |
| Thibetolide | 30 |
| cis-3-Hexenyl salicylate | 30 |
| Hydroxycitronellal | 20 |
| Eugenol | 20 |
| cis-3-Hexenyl benzoate | 20 |
| Methyl jasmonate | 10 |
| β-Ionone | 5 |

-continued

|  | Parts by weight |
|---|---|
| cis-3-Hexenol | 1 |
| cis-3-Hexenyl acetate | 1 |
|  | 970 |

The addition of 30 parts by weight of the cis/trans mixture I'a/I'b (3:2) brings about a very pleasant rounding-off of this perfume composition. The bottom note in the direction "ylang-ylang" is enriched by aspects reminiscent of frangipani flowers (*Plumeria acutifolia*) and tuberose. These positive effects can still be established clearly even after 24 hours.

Example 3

Herb tea composition usable for flavors and for perfume creations (compositions):

|  | Parts by weight |
|---|---|
| Linalool | 210 |
| Anethol | 120 |
| Phenylethyl alcohol | 120 |
| α-Terpineol | 60 |
| Citronellol | 60 |
| Geranylacetone | 60 |
| cis-3-Hexenyl benzoate | 60 |
| Anisaldehyde | 45 |
| Phenylacetaldehyde | 30 |
| Eugenol | 30 |
| Menthol | 30 |
| Estragol | 15 |
| Verbenone | 15 |
| β-Ionone | 9 |
| Citral | 6 |
| Methyl jasmonate | 3 |
| cis-3-Hexenol | 1 |
| Dipropylene glycol | 96 |
|  | 970 |

The addition of 30 parts by weight of the cis/trans mixture I'a/I'b (3:2) confers more warmth and naturalness to this composition. A note, which can be associated with freshly dried alpen herbs, comes into play very advantageously.

Example 4

Flavor with "milky character":

|  | Parts by weight | |
|---|---|---|
|  | a | b |
| Acetoin | 25 | 25 |
| Vanillin | 20 | 20 |
| Maltol | 10 | 10 |
| Diacetyl | 10 | 10 |
| Ethyl lactate | 10 | 10 |
| δ-Decalactone | 10 | 10 |
| Caproic acid | 7 | 7 |
| Ethyl butyrate | 4 | 4 |
| Caprylic acid | 1 | 1 |
| cis- and trans-1'a/1'b | — | 10 |
| Propylene glycol | 903 | 893 |
|  | 1000 | 1000 |

After dilution in sugar syrup solution (20 g of flavor a or b per 100 l of sugar syrup 10° Bx) the two flavors a and b are compared for taste.

Flavor b is clearly preferred by a panel of test persons, since the desired notes reminiscent of cream and condensed milk come into play strongly.

I claim:
1. Substantially pure 5-methyl-6-pentyl-tetrahydro-α-pyrone.
2. Substantially pure cis-5-methyl-6-pentyl-tetrahydro-α-pyrone.
3. trans-5-Methyl-6-pentyl-tetrahydro-α-pyrone.

* * * * *

UNITED STATES PATENT AND TRADEMARK OFFICE
CERTIFICATE OF CORRECTION

PATENT NO. : 5,248,792

DATED : September 28, 1993

INVENTOR(S) : Roman Kaiser

It is certified that error appears in the above-identified patent and that said Letters Patent is hereby corrected as shown below:

At column 1, lines 45-50, Chemical Formula I'b should be as folllows:

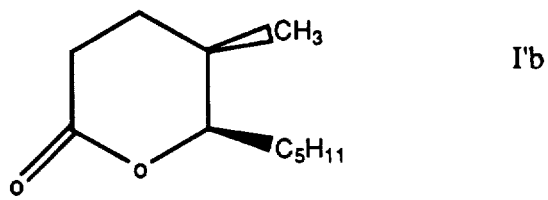   I'b

Signed and Sealed this

Tenth Day of May, 1994

Attest:

BRUCE LEHMAN

Attesting Officer     Commissioner of Patents and Trademarks